(12) United States Patent
Lindner

(10) Patent No.: US 7,585,980 B2
(45) Date of Patent: Sep. 8, 2009

(54) IMMOBILIZED 1,2-BENZISOTHIAZOLIN-3-ONE

(75) Inventor: Wolfgang Lindner, Parsippany, NJ (US)

(73) Assignee: Troy Corporation, Florham Park, NJ (US)

( * ) Notice: Subject to any disclaimer, the term of this patent is extended or adjusted under 35 U.S.C. 154(b) by 0 days.

(21) Appl. No.: 11/440,965

(22) Filed: May 25, 2006

(65) Prior Publication Data

US 2007/0275945 A1      Nov. 29, 2007

(51) Int. Cl.
*C07D 275/04* (2006.01)
(52) U.S. Cl. ...................................... 548/209
(58) Field of Classification Search ................... 548/209
See application file for complete search history.

(56) References Cited

U.S. PATENT DOCUMENTS

| | | | |
|---|---|---|---|
| 3,065,123 A | 11/1962 | Hinton et al. | |
| 4,150,026 A | 4/1979 | Miller et al. | |
| 4,188,376 A | 2/1980 | Payne et al. | |
| 4,871,754 A | 10/1989 | Bauer et al. | |

2007/0275094 A1   11/2007   Thompson et al.

OTHER PUBLICATIONS

W. Paulus, "Directory of Microbiocides For The Protection Of Materials" pp. 664-666 (2005), Springer, Dordrecht.
W. Lindner, "Chemisch-physikalisches Verhalten von Konservierungsmitteln in Beschichtungsstoffen" Band 509.
W. Lindner, "Directory of Microbiocides For The Protection Of Materials" (2005), W. Paulus (ed) Springer.
PCT/US0710124 Report, Jul. 7, 2008.

*Primary Examiner*—Rebecca L Anderson
*Assistant Examiner*—Shawquia Young
(74) *Attorney, Agent, or Firm*—Robert F. Tavares; Robert A. Yesakevich

(57) ABSTRACT

The present invention provides novel antimicrobial immobilized 1,2-benzisothiazolin-3-one/zinc oxide (BIT/ZnO) complexes useful as antimicrobial agents because of their resistance to being leached from the substrate to which they are attached. The present invention is also directed to methods for preparing the BIT/ZnO complexes, to BIT/ZnO complexes prepared by the novel methods, to methods for using the BIT/ZnO complexes to inhibit microbial growth or reduce the level of bacteria on the surface of a substrate, and to substrates protected from microbial attack by being treated with the BIT/ZnO complexes. The present invention is further directed to compositions comprising 1,2-benzisothiazolin-3-one which has been immobilized with zinc oxide.

24 Claims, 4 Drawing Sheets

IMMOBILIZED 1,2-BENZISOTHIAZOLIN-3-ONE

BACKGROUND OF THE INVENTION

1. Field of the Invention

The present invention provides novel antimicrobial immobilized 1,2-benzisothiazolin-3-one/zinc oxide complexes useful as preservatives because of their resistance to being leached from the substrate to which they are attached. This invention also provides substrates having antimicrobial protection including those that require high temperatures in their processing such as, but not restricted to, powder coatings, wood composites and plastics such as polyvinyl chloride (PVC), low-density polyethylene (LDPE), low-density polyethylene foam, plastisols, and polyurethane.

2. Description of the Related Art

Many materials that come into contact with moisture are prone to destructive attacks by a variety of microorganisms including fungi, yeast, algae, and bacteria. Consequently, there is a great need for an effective and economical means to protect such materials from such destructive attacks for extended periods of time. Commercial materials which usually require such protection include, for example, plastics, wood, wood products, wood composites, plastic-wood composites, molded plastics, building materials, paper, toys, coatings, protein-based materials, starch-based compositions, inks, emulsions, resins, stucco, concrete, stone, wood adhesives, caulking, sealants, leather, leather finishes, soap wrappers, packaging materials, spin finishes, fabrics, cordage, carpet backings, electrical insulation, medical devices, and the like.

In addition to protecting commercial materials from such destructive attacks, it is also desirable to inhibit the growth of microorganisms on the surface of the commercial materials to maintain hygienic conditions in, for example, hospitals, nurseries, senior care institutions, food processing facilities, airplanes, trains, buses, and the like.

No single antimicrobial compound provides protection against all microorganisms or is suitable for all applications. In addition to limitations concerning efficacy, other limitations include compound stability, physical properties, toxicological profile, regulatory considerations, economic considerations, and environmental concerns. Antimicrobials that are suitable in many applications may not be suitable in other applications. There is, therefore, a need to develop novel antimicrobial compositions that will provide protection in a variety of applications and under a variety of conditions to protect commercial materials from destructive microorganism attacks and inhibit the growth of microorganisms on the surface of the commercial materials.

A widely used antimicrobial is 1,2-benzisothiazolin-3-one (BIT). BIT and its water-soluble alkali metal salts, are often the biocides of choice when an industrial bactericide is needed to prevent microbial spoilage of water-based technical systems like mineral slurries, polymer emulsions, inks, paints, stucco, adhesives, and the like. (See, for example, W. Paulus "Dictionary of Microbicides for the Protection of Materials" pp. 664-666 (2005), Springer, Dordrecht.)

BIT and its salts are used primarily in liquid systems such as in the coatings industry (paints, varnishes etc.). BIT, and it salts, are used almost exclusively as "in can" preservatives to protect a liquid paint while the paint is in the container before and during application. BIT is not used to protect the coating from microbial growth after it has been applied to the substrate since BIT readily leaches out of the dried coating film.

U.S. Pat. No. 3,065,123 discloses adding 1,2-benzisothiazolin-3-one to an aqueous media to protect the aqueous media from infection by microorganisms. U.S. Pat. No. 4,150,026 discloses metal salt complexes of 3-isothiazolones, which exhibit bactericidal, fungicidal, and algaecidal properties. U.S. Pat. No. 4,188,376 discloses biocidal compositions suitable for indirect food contact applications and in-can preservation of water-based paints comprising a solution of an alkali metal salt of 1,2-benzisothiazolin-3-one in an alcohol, glycol, or water solvent. U.S. Pat. No. 4,871,754 discloses the use of aqueous formulations of the lithium salt of 1,2-benzisothiazolin-3-one to protect aqueous solutions from infestation by microorganisms.

Antimicrobial compounds that are effective as film preservatives, such as Polyphase®, a 3-iodo-2-propynyl butyl carbamate composition, remain in the dried coating and can thereby continue to protect the coating from microbial growth. Polyphase® is mainly effective against fungi and mildew. Accordingly, there is a need for an antibacterial film preservative having the toxicological profile of BIT that will not lose its efficacy over time due to evaporation or leaching. (See W. Lindner in "Chemisch-physikalisches Verhalten von Konservierungsmittel in Beschichtungsstoffen" (1998) Expert Verlag, Bd 509, W. Lindner in "Directory of Microbicides for the Protection of Materials" (2005), W. Paulus (ed) Springer).

SUMMARY OF THE INVENTION

The present invention provides novel antimicrobial immobilized 1,2-benzisothiazolin-3-one/zinc oxide (BIT/ZnO) complexes useful as antimicrobial agents that are resistant to being leached from the substrate to which they are attached. The present invention is also directed to methods for preparing the BIT/ZnO complexes, to BIT/ZnO complexes prepared by the novel methods, to methods for using the BIT/ZnO complexes to inhibit microbial growth or reduce the level of bacteria on the surface of a substrate, and to substrates protected from microbial attack by being treated with the BIT/ZnO complexes. The present invention is further directed to compositions comprising 1,2-benzisothiazolin-3-one which has been immobilized with zinc oxide.

DETAILED DESCRIPTION OF THE INVENTION

Applicants have discovered that the antimicrobial agent 1,2-benzisothiazolin-3-one (BIT) can be immobilized by admixing the antimicrobial agent with an immobilizing effective amount of zinc oxide (ZnO). While not wishing to be bound by theory, applicants believe that the antimicrobial agent and the immobilizing agent are subject to an attractive interaction, which assists in immobilizing the antimicrobial agent from the normally deleterious leaching effects from the substrates to which they are applied. BIT and zinc oxide may form an acid base complex and additional zinc oxide may deposit itself around the BIT/ZnO complex since higher ratios of ZnO to BIT results in a higher tendency of the BIT/ZnO complex to be immobilized. This immobilization retards or prevents leaching of the antimicrobial agent and results in greater retention of the antimicrobial protection in the final substrate than is the case when the immobilizing agent is not present. The combination of the antimicrobial agent and the immobilizing agent works in an unexpected manner to improve the immobilization of the antimicrobial agent on a substrate.

Figure 1:
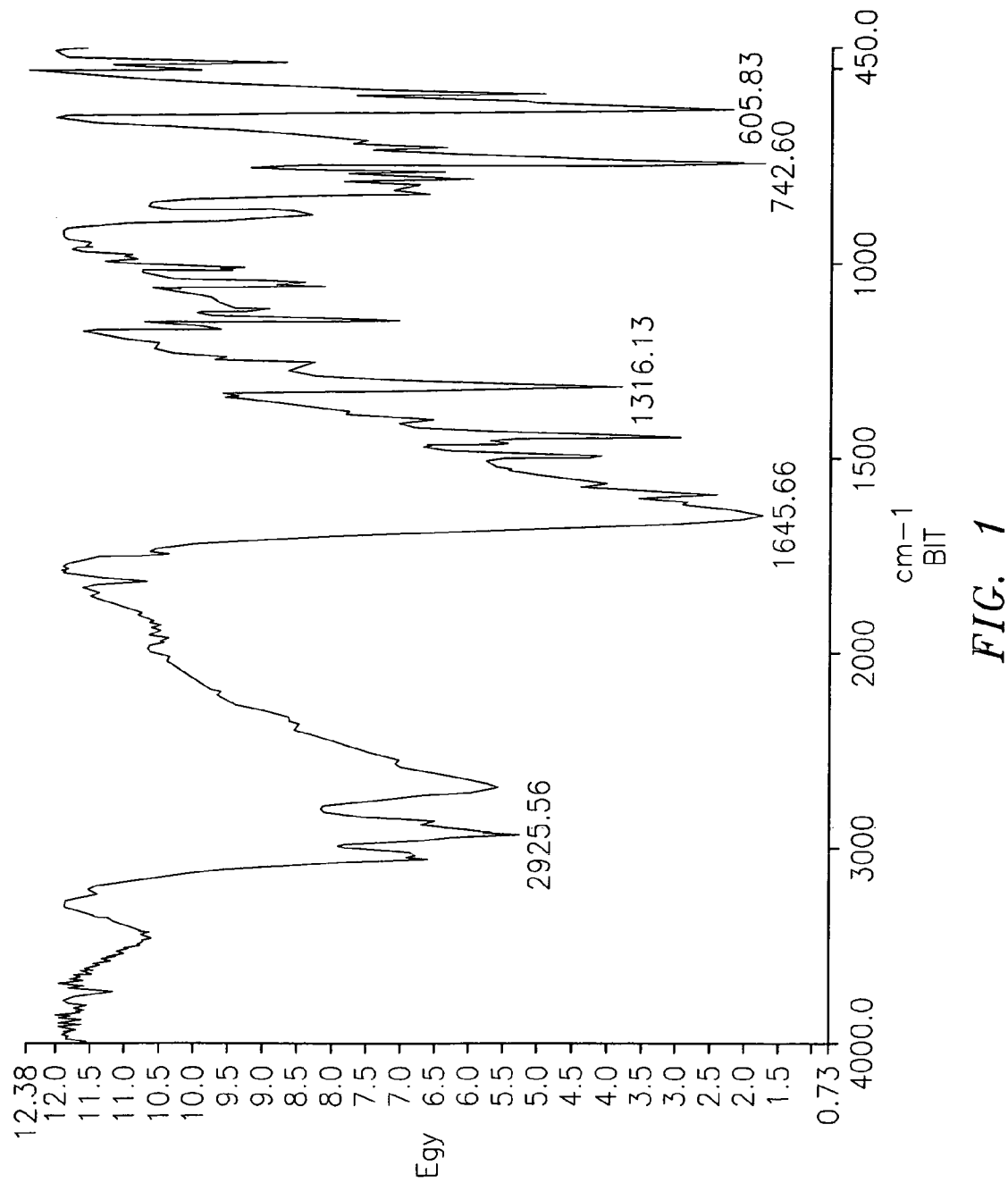
FIG. 1 is a graph showing the infrared spectrum of 1,2-benzisothiazolin-3-one (BIT).
Figure 2:
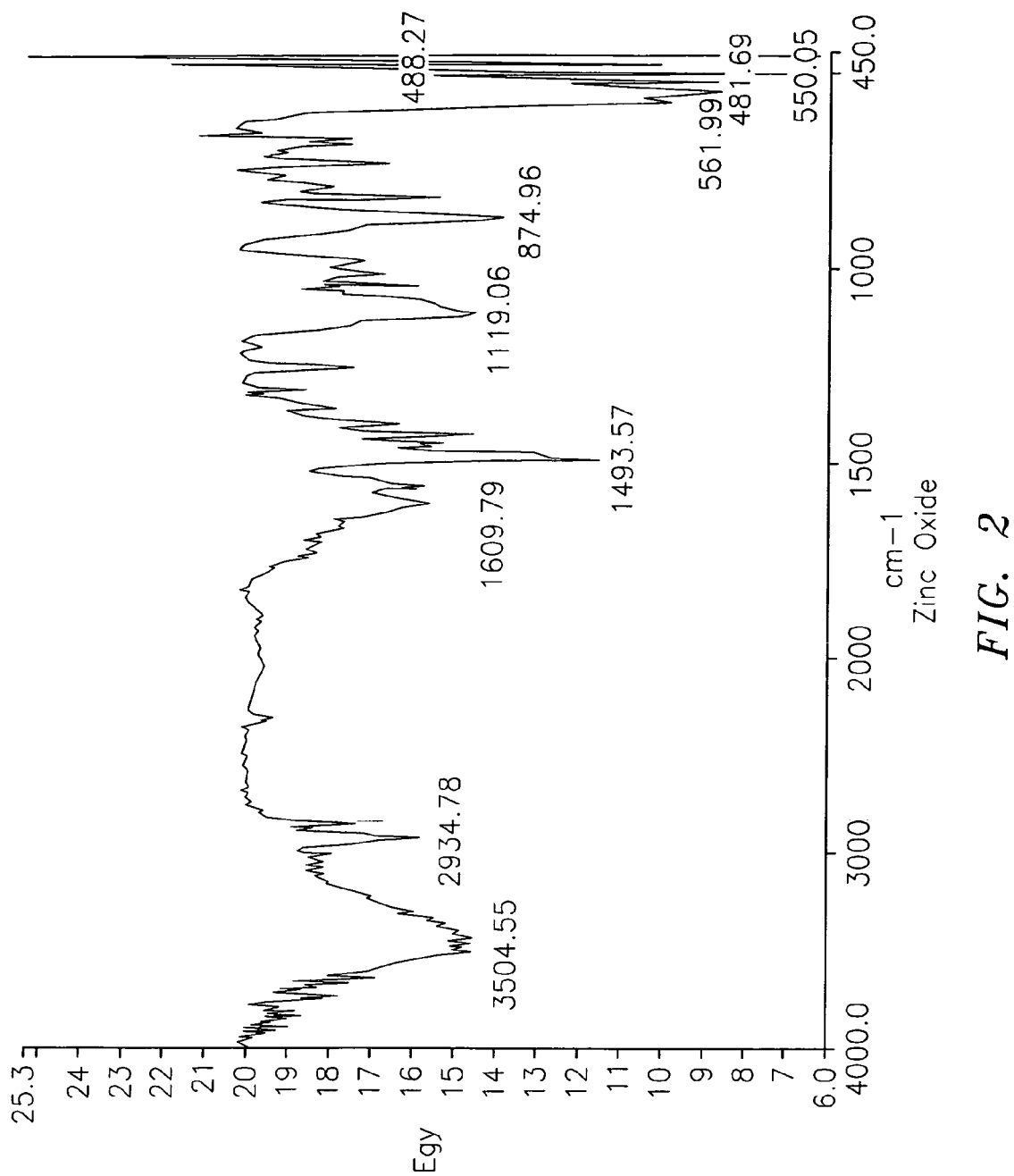
FIG. 2 is a graph showing the infrared spectrum of zinc oxide (ZnO).
Figure 3:
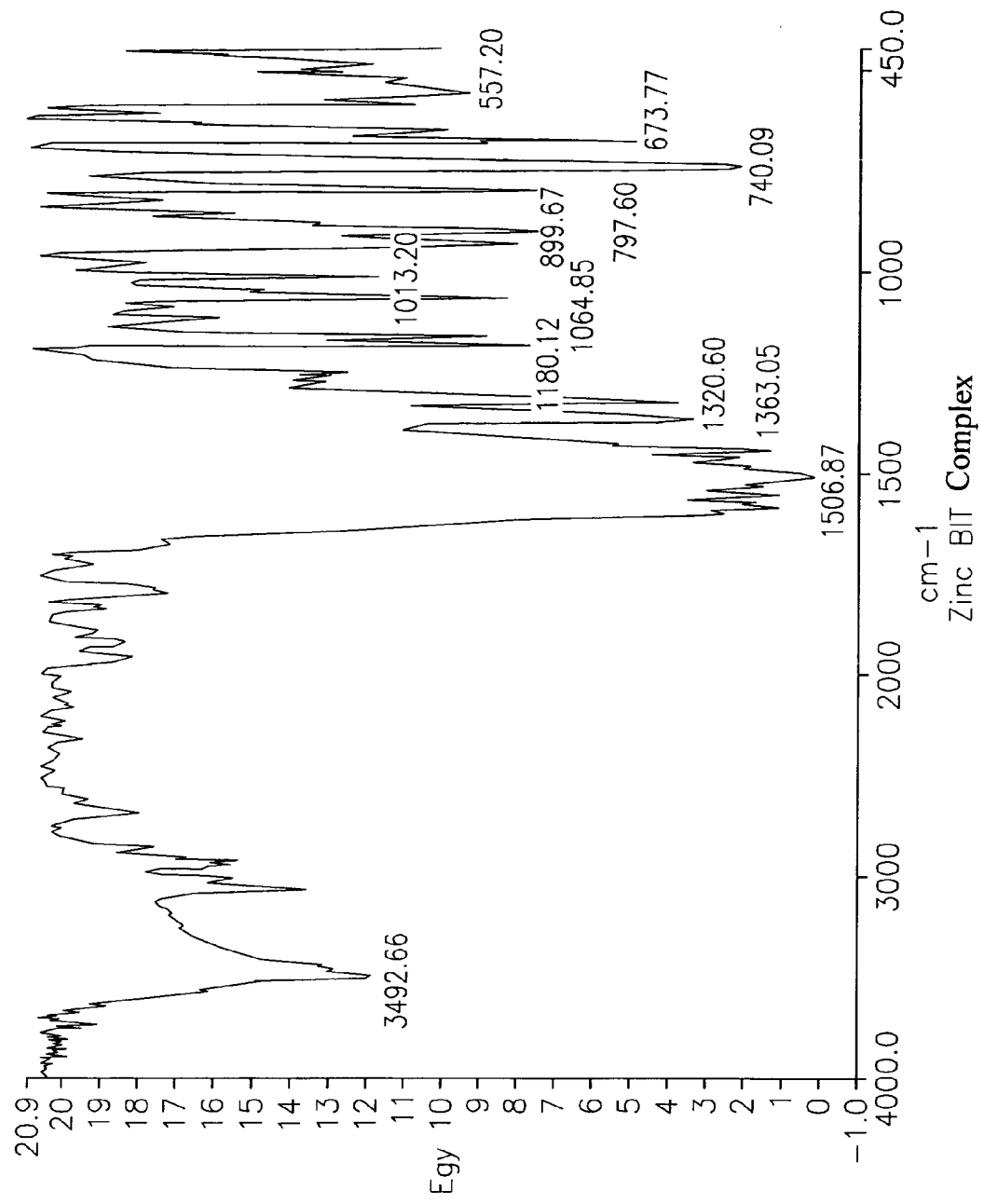
FIG. 3 is a graph showing the infrared spectrum of a BIT/ZnO complex.
Figure 4:
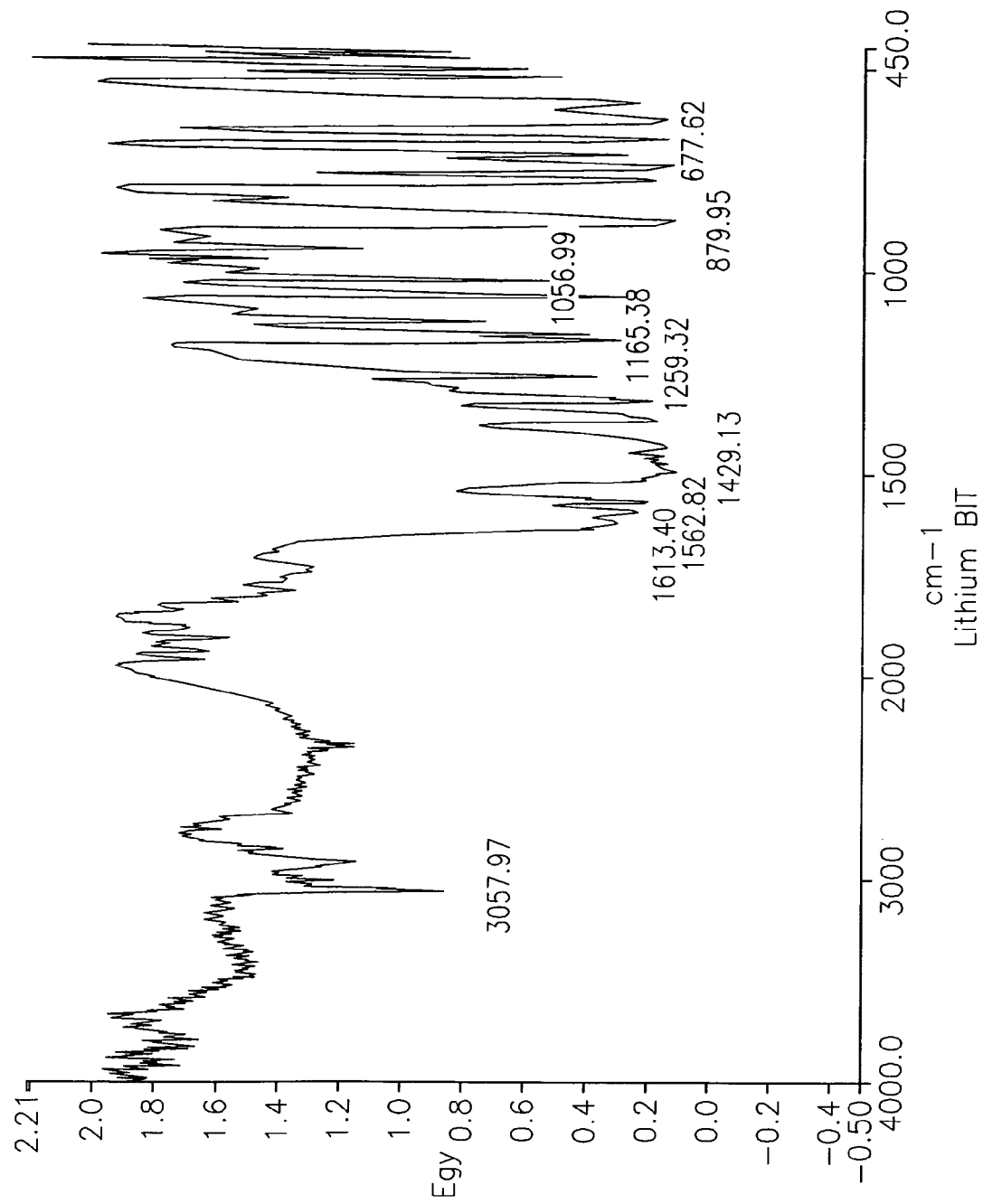
FIG. 4 is a graph showing the infrared spectrum of a BIT/Li salt.

As set out in FIGS. 1-4, the structure of the immobilized BIT/ZnO complex has been analyzed by infrared spectra. FIG. 1 is a graph showing the infrared spectrum of BIT with a strong carbonyl band at 1645 $cm^{-1}$. FIG. 2 is a graph showing the infrared spectrum of ZnO. FIG. 3 is a graph showing the infrared spectrum of a BIT/ZnO complex. FIG. 4 is a graph showing the infrared spectrum of a BIT/Li salt. The infrared spectrum in FIG. 3 clearly shows that the BIT/ZnO complex is not a physical mixture of BIT and ZnO because the carbonyl band of BIT at 1645 $cm^{-1}$ (FIG. 1) is missing. The immobilized BIT/ZnO complex is not an alkali salt, which is apparent by comparison with the infrared spectrum of a BIT/Li salt (FIG. 4). The infrared spectra of the immobilized BIT/ZnO complex and the BIT/Li salt would be expected to be very similar since the same organic anion is involved. But the infrared spectra of the immobilized BIT/ZnO complex and the BIT/Li salt are different especially in the "fingerprint"-region of 700 $cm^{-1}$ to 1400 $cm^{-1}$, which represents the combined resonances of the BIT molecule. In the BIT/Li salt, the bands of the BIT/ZnO complex at 910, 899, and 797$cm^{-1}$ are missing, while in the BIT/ZnO complex the bands of the BIT/Li salt at 1055$cm^{-1}$ and 880$cm^{-1}$ are missing. The infrared spectrum of ZnO (FIG. 2) is void in the infrared range, the bands present are from humidity (approx 3300 $cm^{-1}$) or organic impurities at the high concentration. The combination of the infrared spectra in FIGS. 1-4 together with the HPLC-analysis on methanol-extractable BIT and total BIT after hydrolysis (Examples 2-7) suggest that BIT must be complexed on the ZnO.

BIT may be immobilized on ZnO surfaces by precipitating water-soluble salts of BIT, especially alkali metal salts, onto ZnO. Non-limiting examples of water-soluble zinc salts of BIT include those formed with zinc chloride, zinc bromide, zinc acetate, zinc formate, and zinc nitrate. The procedure to prepare the immobilized BIT/ZnO complexes can vary widely. A water-soluble salt of BIT can be precipitated onto the surface of a preformed zinc oxide by neutralization of the solution. For example, an aqueous solution of BIT-potassium salt can be admixed with ZnO and $ZnCl_2$ and the BIT then precipitated onto ZnO by neutralizing the mixture. Alternatively, BIT and ZnO can be admixed directly to form the BIT/ZnO complex. Further zinc oxide can be precipitated on the preformed BIT/ZnO complexes. By choosing the precipitation conditions, the properties of the antimicrobial compound can be varied. The BIT/ZnO complexes may be prepared as solid materials or as dispersion concentrates using conventional dispersion technologies. The weight-to-weight ratio of BIT to ZnO in the complex may be adjusted to suit the particular application of the final product. The particle size of the BIT/ZnO complex and the viscosity of the BIT/ZnO complex in the dispersion concentrate may also be adjusted to suit the particular application of the final product. Higher weight to weight ratios of ZnO to BIT result in a higher tendency of the BIT/ZnO complex to be immobilized. The particle size of the BIT/ZnO complex can be adjusted by milling and can range from the nano scale (approximately 10 nm) to several hundred microns. In general, the immobilized BIT/ZnO complex is precipitated in a particle size, which is sufficiently small to be used directly in a coating material. The viscosity of the BIT/ZnO complex dispersion concentrate may be adjusted by the addition of a viscosity-adjusting agent. Preferred reaction media are water, lower alcohols such as methanol, ethanol, isopropanol, n-propanol, n-butanol, sec-butanol, tert-butanol, and mixtures thereof. The immobilized BIT/ZnO complex can be isolated by the usual techniques such as filtration or spray drying. The immobilized BIT/ZnO complex can be combined with additional antimicrobial agents and fungicidal film preservatives such as carbendazim (methylbenzimidazol-2-ylcarbamate), 3-iodo-2-propynyl butyl carbamate, zinc pyrithion, triclosan (5-chloro-2-(2,4-dichlorophenoxy)phenol), 2-n-octylisothiazolin-3-one, 4,5-dichloro-2-n-octylisothiazolin-3-one, chlorthalonil (2,4,5,6, tetrachloroisophthalonitril), bethoxazin (3-benzo[b]thien-2-yl-5,6-dihydro-1,4,2-oxathiazine 4-oxide), ziram (zinc bis (dimethyldithiocarbamate), thiram (tetramethylthiuram disulfide), 2-n-butyl-benzisothiazolin-3-one, and silver and silver compounds such as coated silver on zinc oxide AirQual AQ200, commercially available from AirQual, zinc silver zeolithe compounds, commercially available from Ciba, silver chloride on titanium dioxide commercially available from Clariant, and silver (nano-scale silver), commercially available from NANUX.

The antimicrobial immobilized BIT/ZnO complexes of the present invention provide a complex wherein BIT is resistant to evaporation or leaching, or any other process, that would cause the BIT to be depleted from the surface of a substrate. The antimicrobial immobilized BIT/ZnO complexes also provide antibacterial hygienic coatings for surfaces such as in hospitals, senior homes, kindergartens, food producing units, and pharmaceutical facilities. Bacteria coming into contact with such coatings are controlled by the presence of the immobilized antibacterial agent. Such permanent antimicrobial properties can supplement cleansing and disinfections procedures at difficult to reach surfaces. The antimicrobial immobilized complexes can also control biofilm formation on the surface of sealants such as in water supply systems. The antimicrobial immobilized complexes further provide an antimicrobial compound suitable for use in hygienic surfaces that will not be burdened with undesirable properties characteristic of other antibacterial substances used for such purposes. Additional materials which may be coated with the antimicrobial immobilized BIT/ZnO complexes include coatings, plastics, wood products, wood composites, plastic-wood composites, molded plastics, building materials, paper, starch-based compositions, adhesives, stucco, concrete, caulking, sealants, fabrics, and cordage.

In accordance with the present invention, a method is provided for making an immobilized 1,2-benzisothiazolin-3-one/zinc oxide complex comprising the steps of (a) heating 1,2-benzisothiazolin-3-one and zinc chloride to reflux in a $C_1$-$C_4$ branched or unbranched alcohol to form a solution; (b) cooling the solution and adding an immobilizing effective amount of zinc oxide to the solution to form a mixture; (c) heating the mixture to reflux and then cooling the mixture to room temperature; (d) filtering the mixture to obtain the immobilized 1,2-benzisothiazolin-3-one/zinc oxide complex. The method may further comprise washing the solid material with a $C_1$-$C_4$ branched or unbranched alcohol and drying the solid material under vacuum. The $C_1$-$C_4$ branched or unbranched alcohols may be selected from the group consisting of methanol, ethanol, n-propanol, iso-propanol, n-butanol, sec-butanol, and tert-butanol. Preferably, the $C_1$-$C_4$ branched or unbranched alcohols are selected from the group consisting of methanol, ethanol, n-propanol, and iso-propanol, more preferably, the alcohols are methanol or ethanol, and most preferably methanol.

In another embodiment, the present invention provides a method for making a dispersion concentrate of an immobilized 1,2-benzisothiazolin-3-one/zinc oxide complex comprising the steps of (a) forming an aqueous solution of 1,2-benzisothiazolin-3-one and potassium hydroxide having a pH from about 7 to about 8.5; (b) adding zinc chloride and an immobilizing effective amount of zinc oxide to the solution to form a mixture; and (c) milling the mixture to form the dispersion concentrate of immobilized 1,2-benzisothiazolin-3-one/zinc oxide complex. The method may further comprise adding a dispersing agent to the mixture in step (b) and a defoaming agent to the mixture in step (c).

In yet another embodiment, the present invention provides a method for making a dispersion concentrate of an immobilized 1,2-benzisothiazolin-3-one/zinc oxide complex comprising the steps of (a) forming an aqueous mixture of 1,2-benzisothiazolin-3-one, zinc chloride, and an immobilizing effective amount of zinc oxide; (b) adjusting the pH of the mixture from about 7 to about 8.5; and (c) milling the mixture to form the dispersion concentrate of immobilized 1,2-benzisothiazolin-3-one/zinc oxide complex. The method may further comprise adding a dispersing agent to the mixture in step (a) and a defoaming agent to the mixture in step (c).

In still yet another embodiment, the present invention provides a method for making a dispersion concentrate of an immobilized 1,2-benzisothiazolin-3-one/zinc oxide complex comprising the steps of (a) forming an aqueous mixture of 1,2-benzisothiazolin-3-one and an immobilizing effective amount of zinc oxide; and (b) milling the mixture to form the dispersion concentrate of immobilized 1,2-benzisothiazolin-3-one/zinc oxide complex. The method may further comprise adding a dispersing agent to the mixture in step (a) and a defoaming agent to the mixture in step (b).

The present invention also provides an immobilized 1,2-benzisothiazolin-3-one/zinc oxide complex prepared by the methods set out above. The present invention further provides a method for protecting a substrate from antimicrobial infestation which comprises treating the substrate with an antimicrobially effective amount of an immobilized 1,2-benzisothiazolin-3-one/zinc oxide complex prepared by the methods set out above. The present invention still further provides a composition comprising 1,2-benzisothiazolin-3-one, which has been immobilized with zinc oxide.

The antimicrobial agent used in the immobilized BIT/ZnO complexes of the present invention is commercially available 1,2-benzisothiazolin-3-one (1,2-benzisothiazolin-3(2H)-one, BIT), and the salts thereof. BIT has a molecular weight of 151.19, is soluble in hot water and forms water-soluble salts with alkali metals and amines, and is highly soluble in organic solvents especially alcohols and glycols. BIT, and its water-soluble alkali metal salts, are useful to prevent microbial spoilage of water-based technical systems like mineral slurries, polymer emulsions, inks, paints, stucco, adhesives, and the like. BIT is disclosed in U.S. Pat. No. 3,065,123, which disclosure is incorporated herein by reference.

The immobilizing agent used in the immobilized BIT/ZnO complexes of the present invention is commercially available zinc oxide (ZnO). Zinc oxide has a molecular weight of 81.38, exists as a white or yellowish-white, odorless powder, and is practically insoluble in water. Nanostructures of zinc oxide may also be employed. Nanostructures of zinc oxide are disclosed in detail in Materialstoday, June (2004), pp. 26-33, which disclosure is incorporated herein by reference.

In accordance with the present invention, an immobilizing effective amount of ZnO is admixed with BIT to form an immobilized BIT/ZnO complex. An immobilizing effective amount of ZnO is an amount effective to immobilize the antimicrobial agent BIT in the immobilized BIT/ZnO complex. An excess of immobilizing agent has been found to more efficiently immobilize the antimicrobial agent. The appropriate amount of immobilizing agent may depend upon a number of factors including the nature of the substrate to be protected and the conditions and duration of time under which the substrate is used. The appropriate amount of immobilizing agent for a particular purpose can be determined by routine testing of the immobilization of the antimicrobial agent with varying amounts of added immobilizing agent. Methods for assaying the immobility of the antimicrobial agent, such as by HPLC, are known and available to one skilled in the art, and are set out in the example section of this disclosure. Thus, depending on such factors, the weight-to-weight ratio of BIT:ZnO can be very broad. In general, the weight-to-weight ratio of BIT:ZnO will be from about 1:20 to about 3:1. Preferably, the weight to weight ratio of BIT:ZnO will be from about 1:10 to about 3:1, more preferably from about 1:5 to about 1:1, and most preferably from about 1:3 to about 2:3.

For purposes of this invention, "immobilized BIT" and "free BIT" are defined in operational terms based on the fact that BIT per se is soluble in methanol at greater than 5%, i.e., 5 grams of pure BIT will be completely soluble in 100 ml of methanol. When a solid BIT/ZnO complex made in accordance with this invention is shaken at ambient (room) temperature with twenty (20) times its weight of methanol, any BIT that goes into solution, i.e. is not remain attached to the ZnO, is defined as "free" or "not immobilized" BIT while the BIT that remains attached to the ZnO as part of the solid, undissolved BIT/ZnO complex is defined as "immobilized BIT." Accordingly, the difference between the total amount of BIT in the BIT/ZnO complex and the amount of "free" BIT (that is, the amount of BIT soluble in a predetemined amount of methanol) is the amount of "immobilized BIT" in the BIT/ZnO complex.

The HPLC analytical methods described in the examples section of this disclosure provide a convenient way to analyze a BIT/ZnO complex to determine what amount of BIT therein is "free" and what amount of BIT therein is "immobilized". (For example, if a 500 mg sample of a BIT/ZnO complex that was about 33% by weight of BIT shaken with 100 ml of methanol, such a sample would contain have less than 170 mg. of BIT, and if it were all free BIT it would all dissolve in the methanol forming a less than 0.2% solution. Since the solubility of BIT in methanol at ambient temperature is greater than 5%, such an analysis clearly illustrates any immobilization of the BIT in that any BIT that does not dissolve in the methanol is clearly immobilized in the BIT/ZnO complex.

In general, it is desirable to maximize the amount of BIT that is "immobilized BIT" in the BIT/ZnO complex and to minimize the amount of "free BIT" for the purposes of this invention, it being understood that for special circumstances it may be preferable to have mixtures as opposed to maximizing the "immobilized BIT" in the complex. A ZnO /BIT complex wherein from about 40% to about 100% of th BIT is immobilized would be suitable for many applications with about 50% to about 100% being preferable, with about 70% to about 100% being more preferable and with from about 90% to about 100% being most preferable.

In general, the immobilized BIT/ZnO complex is prepared by precipitation in a dispersion concentrate in a particle size, which is sufficiently small to be used directly in a coating material. The desired particle size of the BIT/ZnO complex may depend upon a number of factors including the nature of the substrate to be protected and the conditions and duration of time under which the substrate is used. The particle size of the BIT/ZnO complex can be adjusted by milling, such as in a pearl mill, and can range from the nano scale (approximately 10nm) to several hundred microns. The particle size of the BIT/ZnO complex may range from 0.8 µm 50%/10 µm 95%. Preferably, the particle size of the BIT/ZnO complex may range from 1 µm 50%/8 µm 95%, more preferably from 1.5 µm 50%/6 µm 95%, and most preferably from 2.5 µm 50%/4 µm 95%, The viscosity of the BIT/ZnO complex dispersion concentrate may be adjusted to be used directly in a coating material. The viscosity of the BIT/ZnO complex may depend upon a number of factors including the nature of the coating and the substrate to be protected. The viscosity of the BIT/ZnO complex dispersion concentrate may be adjusted to suit the particular application of the final product. The viscosity of the BIT/ZnO complex dispersion concentrate may be adjusted by the addition of a viscosity-adjusting agent. A preferred viscosity-adjusting agent is xanthan gum (Kelzan®). The viscosity of the BIT/ZnO complex dispersion concentrate may range from about 400 to about 1200 mPas, preferably from about 400 to about 100 mPas, more preferably from about 400 to about 1000 mPas, and most preferably from about 400 to about 900 mPas.

In accordance with the invention, the antimicrobial immobilized BIT/ZnO complex can be included in a final formulation for use in such end use applications as paints, coatings, plastics, wood products, wood composites, plastic-wood composites, molded plastics, building materials, paper, starch-based compositions, adhesives, stucco, concrete, caulking, sealants, fabrics, cordage, textiles, and the like, in a broad range from about 0.004% to 2.0% active concentration. Such compositions can be prepared from highly concentrated compositions of the immobilized complex by appropriate dilution. The optimum useful range is about 0.01% to 1.0% of immobilized complex in the final formulations for such end use systems. With the use of such modified formulations in end use systems, it is possible to protect substrates for extended periods of time against growth from microorganisms.

Compositions of the present invention will generally be formulated by mixing or dispersing the immobilized complex in a selected proportion with a liquid vehicle for dissolving or suspending the active components. The vehicle may contain a diluent, an emulsifier and a wetting agent. Expected uses of the antimicrobial immobilized complex include the protection of aqueous based paints and coatings, adhesives, joint cements, sealants, caulks, printing inks, metal working fluids, polymer emulsions, pigment dispersions, aqueous industrial products, lubricants, caulkings, and the like. The antimicrobial immobilized complex may be provided as liquid mixtures, as wettable powders, dispersions, or in any other suitable product type, which is desirable. In this regard, the composition of the present invention can be provided as a ready-for-use product in the form of aqueous dispersions, oil dispersions, or as a concentrate.

Useful solvents that can be used in the preparation of products comprising the antimicrobial immobilized complex are several glycol ethers and esters like propylene glycol n-butyl ether, propylene glycol tert-butyl ether, 2-(2-methoxymethylethoxy)-tripropylene glycol methyl ether, propylene glycol methyl ether, dipropyleneglycol methyl ether, tripropylenelene glycol methyl ether, propylene glycol n-butyl ether and the esters of the previously mentioned compounds. Other useful solvents are n-methyl pyrrolidone, n-pentyl propionate and dibasic esters of several dicarboxylic acids, and mixtures thereof. The preferred solvents for these products are propylene glycol n-butyl ether, 1-methoxy-2-propanol, and the dibasic isobutyl ester blend of succinic, glutaric and adipic acids.

When preparing formulations of the present invention for specific applications, the composition also will likely be provided with adjuvants conventionally employed in compositions intended for such applications such as organic binding agents, additional antimicrobials, auxiliary solvents, processing additives, fixatives, plasticizers, UV-stabilizers or stability enhancers, water-soluble or water-insoluble dyes, color pigments, siccatives, corrosion inhibitors, antisettlement agents, anti-skinning agents and the like.

The immobilization of BIT on ZnO may be further controlled by adding to the complex basic salts of carboxylic acids, e.g. fatty acids. Preferred fatty acids are benzoic acid, octanoic acid, 2-ethylhexanoic acid, nonanoic acid, decanoic acid, undecanoic acid, decanoic acid, stearic acid, oleic acid, and mixtures thereof.

According to the present invention, substrates are protected from contamination by microorganisms simply by treating the substrate with a composition containing the antimicrobial immobilized BIT/ZnO complex of the present invention. Such treating may involve mixing the composition with the substrate, coating or otherwise contacting the substrate with the composition and the like.

The following examples are presented to illustrate and explain the invention. Unless otherwise indicated, all references to parts and percentages here and throughout the application are based on weight.

EXAMPLES

Analytical Procedure For Determining the Amount of Immobilized BIT in a BIT/ZnO Complex This analysis determines the total amount of BIT and the amount of "free" BIT in a BIT/ZnO complex. The difference between the total amount of BIT in the BIT/ZnO complex and the amount of "free" BIT (that is, the amount of BIT soluble in a predetermined amount of methanol) is defined as the amount of "immobilized BIT" in the BIT/ZnO complex.

1. Analysis of the Total Amount of BIT in a BIT/ZnO Complex.

To analyze the total amount of BIT in a BIT/ZnO complex, the BIT/ZnO complex must be hydrolyzed to liberate the BIT so that it can be analyzed by standard HPLC techniques.

Hydrolysis.

Approximately 200 mg of the immobilized BIT/ZnO complex is weighed exactly (exact weight may vary depending upon the expected total amount of BIT in the complex being analyzed) into a 100 ml flask. A quantity of 20 ml of methanol (HPLC-grade) and 5 ml of hydrochloric acid (1 mol/l) is then added. The flask is heated to about 50° C. for 15 minutes. After being cooled to ambient temperature, the flask is filled with methanol up to the mark of 100 ml. The reaction mixture is then filtered over a 0.25µ membrane filter (e.g., Millipore) and is ready to be injected into an HPLC-column.

| HPLC Conditions | |
|---|---|
| Instrument | Apparatus Shimadzu A6 |
| Column: | Nucleosil 100-5 C18 HD (Macherey-Nagel) |

-continued

| HPLC Conditions | |
|---|---|
| Solvent Gradient Flow: | 1.3 ml/min |
| UV Detector wave length: | 312 nm |
| Eluent A: | water + 5% acetonitrile (vol:vol) |
| Eluent B: | acetonitrile |

| Flow time (min.) | Solvent Gradient* |
|---|---|
| 0.1 | 10% Eluent B + 90% Eluent A |
| 3.0 | 10% Eluent B + 90% Eluent A |
| 8.0 | 70% Eluent B + 30% Eluent A |
| 10.0 | 70% Eluent B + 30% Eluent A |
| 11.0 | 90% Eluent B + 10% Eluent A |
| 12.0 | 90% Eluent B + 10% Eluent A |
| 13.0 | 10% Eluent B + 90% Eluent A |
| 15.0 | 10% Eluent B + 90% Eluent A |
| 17.0 | stop |

*= vol:vol

The total amount of BIT in the BIT/ZnO complex is then determined by comparison to an external standard (150 mg BIT/1 liter methanol).

2. Analysis of "free" BIT.

BIT is very soluble in methanol and can be extracted from the BIT/ZnO complex to determine the amount of "free" BIT.

Approximately 500 mg of the BIT/ZnO complex is weighed exactly (exact weight can vary depending upon the expected "free" BIT content of the complex analyzed) into a 100 ml flask. A quantity of 50 ml of methanol (HPLC-grade) is added. The flask containing the mixture is then ultrasonicated in a water bath for about 15 minutes. After being cooled to ambient temperature, the flask is filled with methanol up to the mark of 100 ml. The reaction mixture is then filtered over a 0.25μ membrane filter (e.g., Millipore) and is ready to be injected into an HPLC-column.

The HPLC-conditions for analysis of the "free" BIT is the same as set out above in part 1. The amount of "free" BIT in the BIT/ZnO complex is then determined by comparison to an external standard (150 mg BIT/1 liter methanol).

Example 1

Comparative Example bis-(1,2-Benzisothiazolin-3-one)zinc(II)chloride

Bis-(1,2-benzisothiazolin-3-one)zinc(II)chloride was prepared according to example 53 of U.S. Pat. No. 4,150,026.

1.5 g of 1,2-benzisothiazolin-3-one (analytical pure grade) was dissolved in 75 ml of absolute methanol. A quantity of 0.68 g zinc chloride was added to provide a clear solution. The solvent was then evaporated under vacuum and the residue was dried. A quantity of 2.1 g of bis-(1,2-benzisothiazolin-3-one)zinc(II)chloride was obtained. The molar ratio of BIT:Zn=2:1.

The 1,2-benzisothiazolin-3-one was not immobilized as a bis-(1,2-benzisothiazolin-3-one)zinc(II)chloride salt complex because the complex is almost completely soluble in methanol. HPLC analysis showed that 63% of the salt complex was 1,2-benzisothiazolin-3-one obtained from the methanol extract.

Example 2

Dispersion Concentrate of BIT/ZnO from BIT-Potassium Salt

A quantity of 300 g of tap water was admixed with 26.7 g of potassium hydroxide prills and 74.1 g of commercially available 1,2-benzisothiazolin-3-one (90%) (available from Aldrich) until a clear solution resulted. A quantity of 270 g of tap water, 40 g of Emulsogen TS 200 (a dispersing agent available from Clariant), 40 g of Atlox® 4913 (a non-ionic dispersant available from Unigema), 155.7 g of zinc oxide (available from Aldrich), and 30.1 g of zinc chloride (available from Aldrich) were then added and the batch was milled in a pearl mill. The foam was controlled by adding 0.5 g of Rhodorsil 416 (a silicon based defoamer available from Rhodia). The pH was 7. The mixture was passed 3 times through a pearl mill to reduce the particle size. The product was adjusted to a viscosity of 420 mPas (Spindle 4, Brookfield) by addition and dispersion of 4 g xanthan gum (Kelzan®) and 59 g of tap water. The ZnO:BIT weight/weight ratio=2.6:1 and the molar ratio BIT:Zn=0.20.

A quantity of 1000 g of (1,2-benzisothiazolin-3-one)zinc oxide was obtained. Particle size distribution: 1.3 micrometer 50%/5.5 micrometer 95%. Analysis: 6.7% total 1,2-benzisothiazolin-3-one by HPLC after acidic hydrolysis (decomposition in 10% hydrochloric acid, neutralize, dilute with methanol, HPLC analysis of BIT). Analysis of soluble BIT from methanol extract: 2.4%. (64% of the total BIT is fixed on the ZnO surface)

Example 3

Dispersion Concentrate of BIT/ZnO from BIT-ZnCl$_2$

A quantity of 90 g of tap water was mixed with 22.2 g of commercially available 1,2-benzisothiazolin-3-one (90%), 12 g of Emulsogen TS 200, 12 g of Atlox® 4913, 46.7 g of zinc oxide, and 9.0 g of zinc chloride. The batch was neutralized to pH 8.5 by slow addition with stirring of 16 g of a 50% (w/w) potassium hydroxide solution. The batch was passed 3 times through a pearl mill to reduce the particle size. Foam was controlled by adding 0.5 g of Rhodorsil 416. The product was then adjusted to a viscosity of 720 mPas (Spindle 3, Brookfield, 100 rpm) by addition and dispersion of 1.6 g of xanthan gum and 121 g of tap water. The ZnO:BIT weight/weight ratio=2.6:1 and the molar ratio BIT:Zn=0.20.

A quantity of 400 g of a dispersion concentrate of (1,2-benzisothiazolin-3-one)zinc oxide was obtained. Particle size distribution: 0.8 micrometer 50%/3.5 micrometer 95%. Analysis: 6.7% total 1,2-benzisothiazolin-3-one by HPLC after acidic hydrolysis (decompose in 10% hydrochloric acid, neutralize, dilute with Methanol, HPLC analysis of BIT). Analysis of soluble BIT from methanol extract: 1.1%. (84% of the total BIT is fixed on the ZnO surface)

Example 4

Dispersion Concentrate of BIT/ZnO from BIT-ZnCl$_2$

A quantity of 90 g of tap water was mixed with 22.2 g of commercially available 1,2-benzisothiazolin-3-one (90%), 12 g of Emulsogen TS 200, 12 g of Atlox® 4913, 20.6 g of zinc oxide, and 9.0 g of zinc chloride. The batch was neutralized to pH 8.5 by admixing 16 g of a 50% (w/w) potassium hydroxide solution. The batch was passed 3 times through a pearl mill to reduce the particle size. Foam was controlled by adding 0.2 g of Rhodorsil 416. The product was then adjusted to a viscosity of 950 mPas (Spindle 3, Brookfield, 100 rpm) by addition and dispersion of 1.8 g xanthan gum and 147 g of tap water. The ZnO:BIT weight/weight ratio=1.6:1 and the molar ratio BIT:Zn=0.35)

A quantity of 400 g of a dispersion concentrate of (1,2-benzisothiazolin-3-one)zinc oxide was obtained. Particle size distribution: 1.3 micrometer 50%/6.0 micrometer 95%. Analysis: 6.7% total 1,2-benzisothiazolin-3-one by HPLC after acidic hydrolysis (decompose in 10% hydrochloric acid, neutralize, dilute with methanol, HPLC analysis of BIT). Analysis of soluble BIT from methanol extract: 1.6%. (76% of the total BIT is fixed on the ZnO surface).

Example 5

Dispersion Concentrate of BIT/ZnO By Direct Precipitation in a Pearl Mill

A quantity of 166.2 g of tap water was mixed with 33.3 g of commercially available 1,2-benzisothiazolin-3-one (90%), 3 g of Emulsogen TS 200, 6 g of Atlox® 4913, and 70.1 g of zinc oxide. The batch was milled in a pearl mill for 30 minutes. Foam was controlled by adding 0.3 g of Rhodorsil 416. The product was then adjusted to a viscosity of 1180 mPas (Spindle 3, Brookfield, 100 rpm) by addition of 0.6 g xanthan gum and 21 g of tap water. The ZnO:BIT weight/weight ratio=2.3:1 and the molar ratio BIT:Zn=0.24.

A quantity of 300 g of a dispersion concentrate of (1,2-benzisothiazolin-3-one)zinc oxide was obtained. Particle size distribution: 2.4 micrometer 50%/10 micrometer 95%. Analysis: 9.9% total 1,2-benzisothiazolin-3-one by HPLC after acidic hydrolysis (decompose in 10% hydrochloric acid, neutralize, dilute with methanol, HPLC analysis of BIT). Analysis of soluble BIT from methanol extract: 2.8%. (72% of the total BIT is fixed on the ZnO surface)

Example 6

Dispersion Concentrate of BIT/ZnO By Direct Precipitation in a Pearl Mill

The product from Example 5 was milled for 4 hours. A quantity of 300 g of a dispersion concentrate of (1,2-benzisothiazolin-3-one)zinc oxide was obtained.

Particle size distribution: 1.0 micrometer 50%/4.5 micrometer 95%. Analysis: 9.8% total 1,2-benzisothiazolin-3-one by HPLC after acidic hydrolysis (decompose in 10% hydrochloric acid, neutralize, dilute with methanol, HPLC analysis of BIT). Analysis of soluble BIT from methanol extract: 0.8%. (92% of the total BIT is fixed on the ZnO surface)

Example 7

Dispersion Concentrate of BIT/ZnO By Direct Precipitation in a Pearl Mill

A quantity of 140 g of tap water was mixed with 6.7 g of commercially available 1,2-benzisothiazolin-3-one (90%), 3 g of Emulsogen TS 200, 6 g of Atlox 4913, and 134 g of zinc oxide. The batch was milled in a pearl mill for 4 hours. Foam was controlled by adding 0.1 g of Rhodorsil 416. The product was then adjusted to a viscosity of 1180 mPas (Spindle 3, Brookfield, 100 rpm) by addition of 0.6 g xanthan gum and 10 g of tap water. The ZnO:BIT weight/weight ratio=20:1 and the molar ratio BIT:Zn=0.028.

A quantity of 300 g of a dispersion concentrate of (1,2-benzisothiazolin-3-one)zinc oxide was obtained. -Particle size distribution: 1.5 micrometer 50%/7.7 micrometer 95%. Analysis: 2.0% total 1,2-benzisothiazolin-3-one by HPLC after acidic hydrolysis (decompose in 10% hydrochloric acid, neutralize, dilute with methanol, HPLC analysis of BIT). Analysis of soluble BIT from methanol extract: 0.1%. (95% of the total BIT is fixed on the ZnO surface)

Example 8

Solid Immobilized BIT/ZnO

A quantity of 30 g (198 mmol) 1,2-benzisothiazolin-3-one and 15 g (110 mmol) of zinc chloride was heated to reflux in 250 ml of methanol. The resulting clear solution was cooled to approximately 50° C. and 70 g (860 mmol) of zinc oxide was added. The mixture was then heated to reflux for 1 hour with stirring and then cooled to room temperature. The solid material was filtered off and washed with 250 ml portions of methanol until no chloride could be detected in the filtrate by testing with silver nitrate in sulfuric acid. The BIT/ZnO complex was dried under vacuum to constant weight to yield 90 g of a white powder. The ZnO:BIT weight/weight ratio=2.57:1 and the molar ratio BIT:ZnO=0.20.

The BIT/ZnO product was analyzed by heating 300 mg at 60° C. for 10 minutes with 50 ml of a 5% solution of sodium hydroxide in methanol. Sufficient methanol was added to bring the solution to 100 ml and the resulting solution was filtered through a 0.45 micron filter and injected into a RP-18 HPLC column (eluent was an acetonitrile/water mixture.) The amount of BIT was determined using an external standard and a UV detector operating at 310 nm. A theoretical yield of 96% based upon BIT was achieved of a BIT/ZnO complex that was tested free of chloride. (96% of the total BIT is fixed on the ZnO surface)

Example 9

Dispersion Concentrate of Immobilized BIT/ZnO from BIT-Potassium Salt

A quantity of 45 g of potassium hydroxide prills, 125 g of 1,2-benzisothiazolin-3-one (80% BIT, Mergal® BIT technical, commercially available from Troy GmbH), and 20 g of Emulsogen TS 200 were mixed in 440 g of tap water until a clear solution was obtained. 234 g of zinc oxide was admixed and 12.5 g of Emulsogen TS 200 was added. The foam was controlled by adding 0.5 g of Rhodorsil 416. 45 g of zinc chloride was then added and the temperature was raised to 40° C. The pH was adjusted to 8 by addition of 30 g hydrochloric acid (16%). The mixture was passed 3 times through a pearl mill to reduce the particle size. The product was adjusted to a viscosity of 440 mPas (Spindle 4, Brookfield) by addition of 2 g xanthan gum. The ZnO:BIT weight/weight ratio=2.6:1 and the molar ratio BIT:ZnO=0.20.

A quantity of 1000 g of (1,2-benzisothiazolin-3-one)zinc oxide was obtained. Particle size distribution: 19 micrometer 50%/79 micrometer 95%. Analysis: 10.0% 1,2-benzisothiazolin-3-one by HPLC after alkaline hydrolysis.

Example 10

Infrared Spectrum of BIT

The BIT sample employed for the infrared spectrum analysis in FIG. 1 was Mergal analytical standard (99.56%) from Troy Corporation. The sample was prepared according to standard procedures as a pressed (10-20%) KBr(99%)-pill using a Perkin-Elmer, System 2000 FT-IR Instrument.

Example 11

Infrared Spectrum of ZnO

The ZnO sample employed for the infrared spectrum analysis in FIG. 2 was analytical grade (99+%). The procedure for conducting the infrared spectrum analysis is the same as set out in Example 10.

Example 12

Infrared Spectrum of BIT/ZnO Complex

The BIT/ZnO sample employed for the infrared spectrum analysis in FIG. 3 was the complex prepared in example 8. The procedure for conducting the infrared spectrum analysis is the same as set out in Example 10.

Example 13

Infrared Spectrum of BIT/Li Salt

The BIT/Li salt sample employed for the infrared spectrum analysis in FIG. 4 was an analytical grade (99%) standard from Mergal. A quantity of 202 g (1 mol) of BIT (Proxel Press Paste, Arch) as a 75% wet cake (remainder water) and 45 g (1.07 mol) of lithium hydroxide-hydrate was heated to reflux for one hour in 700 ml of methanol. The mixture was then cooled to ambient temperature to precipitate the BIT-lithium salt, which was isolated by filtration and dried to constant weight. The procedure for conducting the infrared spectrum analysis is the same as set out in Example 10.

Example 14

Activity of the Immobilized BIT/ZnO Complex in a Water-Based Flat Paint Against *Pseudomonas aeruginosa* Using a Modified Swiss Standard SNV195120 Test The activity of the immobilized BIT/ZnO complex from Example 8 as a dry-film bactericide against *Pseudomonas aeruginosa* DSM 939 was determined in an ICI UK, Diamond Matt paint, a commercially available water-based interior flat paint (40% acrylic binder) according to the modified Swiss Standard SNV195120, which is described below Preparation of Test Specimen:

The immobilized BIT/ZnO complex from example 8 was incorporated into the water-based interior flat paint at the levels shown in the Table below. The paints were allowed to equilibrate for one week at room temperature.

A quantity of 50 mg of the BIT/ZnO complex was mixed with 100 g of the paint (resulting in 0.05% of the specimen 1 in the table below, the other specimens were prepared accordingly). Round filter papers (5.5 cm diameter) were coated with the test material to a thickness of 150 g/m2 wet and the resulting specimens dried at room temperature.

One half of the test specimen was leached by tap water (9 liters per $m^2$) in a beaker. The specimens were dried at room temperature and sterilized by gamma radiation from a cobalt 60 source (25 kGy). In the microbiological test, *Pseudomonas aeruginosa* DSM 939 was used as the bacteria source.

Liquid cultures of each bacterial strain were incubated over night at appropriate temperatures and then diluted 1:100,000 to result in a count of 104 cfu per ml. 0.1ml of these diluted cultures were streaked onto bacterial nutrient in Petri dishes. The test specimens were placed coated side downwards on the inoculated nutrient and incubated for 1 day at 29° C.

The growth of the bacteria on the agar under the test specimen was rated as follows:

0H No bacterial growth under the specimen, inhibition zone on the nutrient.
0 No growth of bacteria under the specimen.
G Growth of bacteria under the specimen.

Bacterial growth under the specimen was seen under the unprotected blank material. Bactericidal protection is provided if there is no growth of bacteria under the specimen.

| Sample No | Sample indication | Antimicrobial Active Conc. % | Film weight (g/m2) | Psa unleached | Psa leached 24 h | Remarks |
|---|---|---|---|---|---|---|
| 1 | Interior flat paint** + 0.05% of immobilized BIT/ex. 8 | BIT* 0.016% | 182 | 0 | G | |
| 2 | Interior flat paint** + 0.1% of immobilized BIT/ex. 8 | BIT* 0.032% | 212 | 0 | 0 | |
| 3 | Interior flat paint** + Thiram | Thiram 0.1% | 223 | 0 | G | Comparative Example |
| 4 | Interior flat paint** + Thiram | Thiram 0.2% | 195 | 0 | G | Comparative Example |
| 5 | Interior flat paint + Ziram | Ziram 0.1% | 209 | 0 | G | Comparative Example |
| 6 | Interior flat paint** + Ziram | Ziram 0.2% | 186 | 0H | G | Comparative Example |
| 7 | Interior flat paint** - blank | none | 255 | G | G | Growth control |

*BIT = 1,2-benzisothiazolin-3-one total concentration
**Interior flat paint = ICI UK, Diamond Matt
Thiram = tetramethylthiuram disulfide
Ziram = (T-4)-bis(dimethyldithio-carbamate-S,S')zinc)

This test demonstrated the efficacy of the immobilized BIT/ZnO complex from Example 8 in very low concentration against *Pseudomonas aeruginosa* in a water-based interior flat paint (40% acrylic binder) using the modified Swiss Standard SNV195120 Test. The effect was still present after an artificial aging process (24 hours leached, submersed in water), demonstrating the durability of the antimicrobial substrate with immobilized 1,2-benzisothiazolin-3-one, while conventionally protected paint samples failed after leaching.

Example 15

Activity of the Immobilized BIT/ZnO Complex in a Water-Based Eggshell Paint Against *Pseudomonas aeruginosa* Using a Modified Swiss Standard SNV195120 Test The activity of the immobilized BIT/ZnO complex from Example 8 as a dry-film bactericide against *Pseudomonas aeruginosa* DSM 939 was determined in a commercially available water-based interior eggshell paint (40% acrylic binder with an adhesion promoter) according to the modified Swiss Standard SNV195120. The composition of the paint, which is typically applied in wet rooms, is set out below.

| Component | Amount |
|---|---|
| Water | 16 g |
| Hydroxymethylcellulose | 0.2 g |
| Calgon N | 0.1 g |
| Titanium dioxide (Rutil) | 15 g |
| Magnesium aluminum silicate | 3 g |
| China clay B | 5 g |
| Calcium carbonate Calcit | 12.5 g |
| Iron oxide | 3 g |
| Mowilith DM 772 (Polyacrylate dispersion Celanese (formerly Clariant) | 40 g |
| Texanol | 4 g |
| Mergal K14 (in-can preservative) | 0.2 g |
| pH was adjusted to 8.5 with Ammonium Hydroxide (25%) | |

The microbiological test was performed according to the procedure described in Example 14.

This test demonstrated the efficacy of the immobilized BIT/ZnO complex from Example 8 in very low concentration against *Pseudomonas aeruginosa* in a water-based interior eggshell paint (40% acrylic binder with an adhesion promoter) using the modified Swiss Standard SNV195120 Test.

Example 16

Activity of the Immobilized BIT/ZnO Complex in a Water-Based Flat Paint Against *Escherichia coli* Using a JIS Z2801:2000 (E) Test The activity of the immobilized BIT/ZnO complex from Example 9 as a dry-film bactericide against *Escherichia coli* was determined in ICI UK, Diamond Matt paint, a commercially available water-based interior flat paint (40% acrylic binder) according to the JIS Z2801:2000 (E) test (Japanese Industrial Standard Z2801:2000 (E) test, Antimicrobial products—Test for antimicrobial activity and efficacy).

The complex was coated on to Leneta Scrub Resistance test panels, with a dry film thickness of 200 micrometers, with a foam roller allowing a drying time of 18 hours between coats. The panels were equilibrated in the dark for 7 days. Sub-samples were cut (each 50 mm×50 mm). The samples were inoculated with a suspension of the test bacteria and then incubated in chambers (1 per species) at 20° C. and 65% relative humidity.

Swabs were employed for recovery of the bacteria. From the blank sample $1.8 \times 10^5$ cfu/cm² were recovered. This number was taken as the starting bacterial load on the surface.

| Sample No | Sample indication | Antimicrobial Active Conc. % | Film weight (g/m2) | Psa unleached | Psa leached 24 h | Remarks |
|---|---|---|---|---|---|---|
| 1 | Interior Paint Eggshell + 0.05% of immobilized BIT/ex 8 | BIT* 0.016% | 229 | G | 0 | Water-soluble growth supporting paint ingredients are washed out. |
| 2 | Interior Paint Eggshell + 0.1% of immobilized BIT/ex 8 | BIT* 0.032% | 231 | 0 | 0H | |
| 3 | Interior Paint Eggshell + Thiram | Thiram 0.1% | 221 | G | G | Comparative Example |
| 4 | Interior Paint Eggshell + Thiram | Thiram 0.2% | 222 | G | G | Comparative Example |
| 5 | Interior Paint Eggshell-blank | | 221 | G | G | Growth control |

*BIT = 1,2-benzisothiazolin-3-one total concentration
Thiram = tetramethylthiuram disulfide

| Sample No | Sample indication | Antimicrobial Active Conc. % | Contact time hrs | Log (Cfu/cm$^2$) | Kill rate % related to blank paint | Remarks |
|---|---|---|---|---|---|---|
| 1a | Interior Paint - blank | blank | 0 | 5.26 | | Recovered inoculum control |
| 1b | Interior Paint - blank | blank | 8 | 5.20 | 0% | |
| 2 | Interior Paint + 0.15% of immobilized BIT/ex. 9 | BIT* 0.05% | 8 | 2.57 | 99.8% | |
| 3 | Interior Paint + 0.05% of ZPT | ZPT 0.05% | 8 | 3.76 | 96.4% | Comparative Example |
| 4 | Interior Paint 2.5% of IPBC-dispersion | IPBC 1.0% | 8 | 5.04 | 31.3% | Comparative Example |

ZPT = Zinc Pyrithione
IPBC = dispersion: 40% 3-Iodopropinoxy-buylacarbamate suspension concentrate
*BIT = 1,2-benzisothiazolin-3-one total concentration This test demonstrated the efficacy of the immobilized BIT/ZnO complex from Example 9 in very low concentration against *Escherichia coli* in a water-based interior flat paint (40% acrylic binder) using the JIS Z2801:2000 (E) Test. The data show that *Escherichia coli* did survive for 8 hours on the water-based interior flat paint (40% acrylic binder) not treated with the immobilized BIT/ZnO complex. The immobilized BIT/ZnO complex reduced the bacteria level by 99.8% while the commercially available comparative materials were significantly inferior.

Example 17

Activity of the Immobilized BIT/ZnO Complex in a Water-Based Flat Paint Against *Pseudomonas aeruginosa* Using a JIS Z2801:2000 (E) Test The activity of the immobilized BIT/ZnO complex from Example 8 as a dry-film bactericide against *Pseudomonas aeruginosa* DSM 939 was determined in ICI UK, Diamond Matt paint, a commercially available water-based interior flat paint (40% acrylic binder) according to the JIS Z2801:2000 (E) test. The microbiological test was performed according to the procedure described in Example 16.

ZPT=Zinc Pyrithione

IPBC=dispersion: 40% 3-lodopropinoxy-buylacarbamate suspension concentrate

*BIT=1,2-benzisothiazolin-3-one total concentration

This test demonstrated the efficacy of the immobilized BIT/ZnO complex from Example 8 in very low concentration against *Pseudomonas aeruginosa* in a water-based interior flat paint (40% acrylic binder) using the JIS Z2801:2000 (E) test.

| Sample No | Sample indication | Antimicrobial Active Conc. % | Contact time hrs | Log (Cfu/cm$^2$) | Kill rate % related to blank paint | Remarks |
|---|---|---|---|---|---|---|
| 1a | Interior Paint - blank | blank | 0 | 5.11 | — | Recovered inoculum control |
| 1b | Interior Paint - blank | blank | 8 | 4.69 | 0% | |
| 2 | Interior Paint + 0.15% of immobilized BIT/ex 8 | BIT* 0.05% | 8 | 3.56 | 92.70% | |
| 3 | Interior Paint + 0.05% of ZPT | ZPT 0.05% | 8 | 4.18 | 69.40% | Comparative Example |
| 4 | Interior Paint 2.5% of IPBC-dispersion* | IPBC 1.00% | 8 | 4.53 | 30.60% | Comparative Example |

Example 18

Activity of the Immobilized BIT/ZnO Complex in a Water-Based Flat Paint Against *Pseudomonas aeruginosa* Using a JIS Z2801 Test

| Sample No | Sample indication | Antimicrobial Active Conc. % | Contact time hrs | Log (Cfu/cm$^2$) | Kill rate % related to blank paint | Remarks |
|---|---|---|---|---|---|---|
| 1a | Interior wall paint - blank | Blank | 0 | 4.18 | — | Recovered inoculum control |
| 1b | Interior wall paint - blank | Blank | 8 | 4.69 | 0% | |

-continued

| Sample No | Sample indication | Antimicrobial Active Conc. % | Contact time hrs | Log (Cfu/cm$^2$) | Kill rate % related to blank paint | Remarks |
|---|---|---|---|---|---|---|
| 2 | Interior wall paint + 0.15% of immobilized BIT/ex 8 | BIT* 0.05% | 8 | 1.08 | 99.98% | |
| 3 | Interior wall paint + 0.05% of ZPT | ZPT 0.05% | 8 | 4.66 | 39.5% | Comparative Example |
| 4 | Interior wall paint 0.25% of IPBC-dispersion* | IPBC 0.1% | 8 | 4.34 | 71.1% | Comparative Example |

The activity of the immobilized BIT/ZnO complex from Example 8 as a dry-film bactericide against *Pseudomonas aeruginosa* DSM 939 was determined in the paint described in example 15 according to the JIS Z2801 test. The microbiological test was performed according to the procedure described in Example 16.

ZPT=Zinc Pyrithione

IPBC=dispersion: 40% 3-Iodopropinoxy-buylacarbamate suspension concentrate

*BIT=1,2-benzisothiazolin-3-one total concentration

This test demonstrated the efficacy of the immobilized BIT/ZnO complex from Example 8 in very low concentration against *Pseudomonas aeruginosa* in an interior acrylic wall paint using the JIS Z2801.

Example 19

Activity of the Immobilized BIT/ZnO Complex in a Water-Based Flat Paint Against *Pseudomonas aeruginosa* Using a JIS Z2801 Test Simulating Severe Environmental Conditions The activity of the immobilized BIT/ZnO complex from Example 8 as a dry-film bactericide after aging against *Pseudomonas aeruginosa* DSM 939 was determined in the paint described in example 15 according to the JIS Z2801 test. The microbiological test was performed according to the procedure described in Example 16. After equilibration, the specimens were leached in water (24 hours) to simulate use conditions in a severe environment. The paint film was cleaned by water jet.

| Sample No | Sample indication | Antimicrobial Active Conc. % | Contact time hrs | Log (Cfu/cm$^2$) | Kill rate % related to blank paint | Remarks |
|---|---|---|---|---|---|---|
| 1a | Interior wall paint - blank | blank | 0 | 4.18 | | Recovered inoculum |
| 1b | Interior wall paint - blank | blank | 24 | 3.88 | 0% | control |
| 2 | Interior wall paint + 0.15% of immobilized BIT/ex. 8 | BIT* 0.05% | 24 | 2.52 | 95.7% | |
| 3 | Interior wall paint + 0.05% of (ZPT) | ZPT 0.05% | 24 | 3.04 | 85.5% | Comparative Example |
| 4 | Interior wall paint 0.25% of IPBC-dispersion* | IPBC 0.1% | 24 | 3.76 | 25.0% | Comparative Example |

ZPT = Zinc Pyrithione
IPBC = dispersion: 40% 3-Iodopropinoxy-buylacarbamate suspension concentrate
*BIT = 1,2-benzisothiazolin-3-one total concentration This test demonstrated the efficacy of the immobilized BIT/ZnO complex from Example 8 in very low concentration against *Pseudomonas aeruginosa* in an interior acrylic wall paint using the JIS Z2801 test simulating severe environmental conditions.

Example 20

Activity of the Immobilized BIT/ZnO Complex in a Water-Based Flat Paint Against *Escherichia coli* Using a JIS Z2801 Test Simulating Severe Environmental Conditions The activity of the immobilized BIT/ZnO complex from Example 8 as a dry-film bactericide after artificial aging against *Escherichia coli* was determined in ICI UK, Diamond Matt paint, a commercially available water-based interior flat paint (40% acrylic binder) according to the JIS Z2801 test. The paint specimens were prepared as described in example 19. The microbiological test was performed according to the procedure described in Example 16. After equilibration, the specimens were leached in water (24 hours) to simulate use conditions in a severe environment. The paint film was cleaned by water jet.

| Sample No | Sample indication | Antimicrobial Active Conc. % | Contact time hrs | Log (Cfu/cm$^2$) | Kill rate % related to blank paint | Remarks |
|---|---|---|---|---|---|---|
| 1a | Interior wall paint - blank | blank | 0 | 3.04 | | Recovered inoculum |
| 1b | Interior wall paint - blank | blank | 24 | 3.30 | 0% | control |
| 2 | Interior wall paint + 0.15% of immobilized BIT/ex 8 | BIT* 0.05% | 24 | 2.73 | 73% | |
| 3 | Interior wall paint + 0.05% of ZPT | ZPT 0.05% | 24 | 3.04 | 20% | Comparative Example |
| 4 | Interior wall paint 0.25% of IPBC-dispersion* | IPBC 0.1% | 24 | 3.76 | 35% | Comparative Example |

ZPT = Zinc Pyrithione
IPBC = dispersion: 40% 3-Iodopropinoxy-buylacarbamate suspension concentrate
*BIT = 1,2-benzisothiazolin-3-one total concentration This test demonstrated the efficacy of the immobilized BIT/ZnO complex from Example 8 in very low concentration against *Escherichia coli* in a water-based interior flat paint (40% acrylic binder) using the JIS Z2801 test simulating severe environmental conditions.

Example 21

Leaching of Immobilized BIT/ZnO Complex in a Water-Based VOC Paint

A water-based low-volatile organic compound (VOC) paint was prepared according to the following formula:

| Ingredient: | % weight | comment |
|---|---|---|
| Water | 21.75 | |
| Walocel XM 30,000 PV | 0.20 | MHEC modified |
| Calgon N neu | 0.20 | Polyphosphate |
| Sodium hydroxide 25% | 0.10 | pH-regulator |
| Borchigel 76 | 0.25% | |
| Borchigen NA40 | 0.50% | |
| Kronos 2160 | 10.00% | Rutil pigment |
| Finntalc M 30 SL | 5.00% | Extender |
| China Clay | 4.00% | Extender |
| Omyacarb 10 GU | 19.60% | Extender |
| Omyacarb 5 GU Mill base 30 min at 2000 cycles/min | 10.00% | Extender |
| Mowilith LDM 1871 | 23.00% | Binder-Vinyl-Ethylene-copolymer |
| Water | 5.40% | |

Preparation of Test Specimen:

The immobilized BIT complex from example 9 (10% BIT) was incorporated as the last component in the paint at the levels indicated in the Table below. As a comparative compound, a commercially available solution of BIT-Lithium (Mergale® K10N) was incorporated into the paint (samples 2 and 4) in the same manner. The test paints were allowed to equilibrate for one week at room temperature. Round filter paper (5.5 cm diameter) was coated with the test paints and the resulting specimens dried at room temperature. The test specimens were leached by tap water (9 liters per m2) in a beaker. After the times indicated in the Table below, test specimens were taken and dried at room temperature. The total BIT concentration in the test paint films was analyzed by HPLC after an alkaline hydrolysis and extraction of the leached paint films.

| Specimen No | Antimicrobial added to the paint | Antimicrobial active substance BIT wt-%/wt wet paint | 8 h Leach-% BIT* | 24 h Leach-% BIT* | Comment |
|---|---|---|---|---|---|
| 1 | 0.3% of immobilized BIT ex. 9 | 0.03% | 42 | 17 | |
| 2 | 0.3% of a water solution of 10% BIT lithium salt | 0.03% | 2 | 1 | Comparative Example |
| 3 | 0.5% of immobilized BIT ex. 9 | 0.05% | 49 | 24 | |
| 4 | 0.5% of a water solution of 10% BIT lithium salt | 0.05% | 1 | 1 | Comparative Example |

The results are expressed as % of the amount found from the original ("unleached") paint sample. This eliminates the error from the variances in extraction method and recovery rates.

This example demonstrates the immobilization of the BIT/ZnO complex in a water-based VOC paint film.

Example 22

Leaching of the Immobilized BIT/ZnO Complex in an Alkyd-Acrylic Binder Paint

The test paint was commercially available Larco Type 147 (Denmark), a water reducible top coat for wooden surfaces based on an alkyd-acrylic hybrid binder. The immobilized BIT complex from example 9 was incorporated into the paint and the paint film test specimens were prepared as described in example 21. After equilibration, the paint specimens were leached as described in example 21. The leaching water was exchanged after 24 hours.

| Specimen No | Antimicrobial | Antimicrobial active substance BIT wt-%/wt wet paint | 24 h Leach-% BIT* | 48 h Leach-% BIT* | Comment |
|---|---|---|---|---|---|
| 1 | 0.3% of immobilized BIT ex. 9 | 0.03% | 50 | 27 | |
| 2 | 0.3% as water solution of 10% BIT lithium salt | 0.03% | 7 | 0 | Comparative Example |
| 3 | 0.5% of immobilized BIT ex. 9 | 0.05% | 47 | 36 | |
| 4 | 0.5% as water solution of 10% BIT lithium salt | 0.05% | 10 | 2 | Comparative Example |

This example demonstrates the immobilization of the BIT/ZnO complex in a commercially available water reducible topcoat paint for wooden surfaces based on an alkyd-acrylic hybrid binder.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

We claim:

1. An immobilized 1,2-benzisothiazolin-3-one/zinc oxide complex prepared by a method comprising the steps of:
    (a) heating 1,2-benzisothiazolin-3-one and zinc chloride to reflux in a $C_1$-$C_4$ branched or unbranched alcohol to form a solution;
    (b) cooling the solution from step (a) and adding an immobilizing effective amount of zinc oxide to the solution to form a mixture;
    (c) heating the mixture from step (b) to reflux and then cooling the mixture to room temperature;
    (d) filtering the mixture from step (c) to obtain a solid material which is the immobilized 1,2-benzisothiazolin-3-one/zinc oxide complex.

2. The complex prepared by the method of claim 1, wherein the weight to weight ratio of 1,2-benzisothiazolin-3-one:zinc oxide is from about 1:20 to about 3:1.

3. An immobilized 1,2-benzisothiazolin-3-one/zinc oxide complex prepared by a method comprising the steps of:
    (a) forming an aqueous mixture of 1,2-benzisothiazolin-3-one and an immobilizing effective amount of zinc oxide; and
    (b) milling the mixture from step (a) to form the dispersion concentrate of immobilized 1,2-benzisothiazolin-3-one/zinc oxide complex.

4. The complex prepared by the method of claim 3, wherein the weight to weight ratio of 1,2-benzisothiazolin-3-one:zinc oxide is from about 1:20 to about 3:1.

5. An immobilized 1,2-benzisothiazolin-3-one/zinc oxide complex prepared by a method which comprises:
    providing a mixture which includes an immobilizing effective amount of zinc oxide; a liquid phase including water or a $C_1$-$C_4$ branched or unbranched alcohol; and an antimicrobial agent dissolved in the liquid phase and selected from the group consisting of 1,2-benzisothiazolin-3-one, salts of 1,2-benzisothiazolin-3-one, and mixtures thereof; and
    precipitating the antimicrobial agent to produce an immobilized 1,2-benzisothiazolin-3-one/zinc oxide complex.

6. The complex prepared by the method of claim 5, wherein the weight to weight ratio of the antimicrobial agent:zinc oxide is from about 1:20 to about 3:1.

7. The complex prepared by the method of claim 6, wherein the weight to weight ratio of the antimicrobial agent:zinc oxide is from about 1:5 to about 1:1.

8. The complex prepared by the method of claim 5, wherein the liquid phase includes water.

9. The complex prepared by the method of claim 8, wherein the liquid phase has a pH of about 7 to about 8.5.

10. The complex prepared by the method of claim 5, wherein the mixture includes a zinc compound selected from the group consisting of zinc chloride, zinc bromide, zinc acetate, zinc formate, and zinc nitrate and mixtures thereof.

11. The complex prepared by the method of claim 10, wherein the mixture includes zinc chloride.

12. The complex prepared by the method of claim 5, which is in the form of particles having a particle size distribution in the range of about 0.8 micrometer 50%/3.5 micrometer 95% to about 19 micrometer 50%/79 micrometer 95%.

13. The complex prepared by the method of claim 5, wherein the liquid phase includes methanol, ethanol, isopropanol, n-propanol, n-butanol, or sec-butanol, and the antimicrobial agent is precipitated by cooling the mixture.

14. The complex prepared by the method of claim 5, which when recovered in solid form includes at least about 40% immobilized 1,2-benzisothiazolin-3-one.

15. The complex prepared by the method of claim 5, which has an infared spectrum that includes bands at 910, 899 and 797 $cm^{-1}$.

16. The complex prepared by the method of claim 15, in which the infared spectrum does not include a band at 1645 $cm^{-1}$.

17. The complex prepared by the method of claim 16, in which the infared spectrum does not include a band at 1055 or 880 $cm^{-1}$.

18. The complex prepared by the method of claim 5, in which the antimicrobial agent is precipitated by cooling, neutralizing or milling the mixture.

19. The complex prepared by the method of claim 16, in which the antimicrobial agent is precipitated by cooling or neutralizing the mixture.

20. The complex prepared by the method of claim 16, in which the antimicrobial agent is precipitated by milling the mixture.

21. An immobilized 1,2-benzisothiazolin-3-one/zinc oxide complex prepared by a method comprising:
    providing a mixture including 1,2-benzisothiazolin-3-one, zinc chloride, an immobilizing effective amount of zinc oxide, and a liquid phase which includes a $C_1$-$C_4$ branched or unbranched alcohol; and
    cooling the mixture and recovering a solid material which includes the immobilized 1,2-benzisothiazolin-3-one/zinc oxide complex.

22. An immobilized 1,2-benzisothiazolin-3-one/zinc oxide complex prepared by a method comprising:
    providing a mixture including zinc chloride, an immobilizing effective amount of zinc oxide, and an aqueous solution having a pH from about 7 to about 8.5 which includes 1,2-benzisothiazolin-3-one; and
    milling the mixture to produce a dispersion concentrate including the immobilized 1,2-benzisothiazolin-3-one/zinc oxide complex.

23. An immobilized 1,2-benzisothiazolin-3-one/zinc oxide complex prepared by a method comprising:
    providing an aqueous mixture including water, 1,2-benzisothiazolin-3-one and an immobilizing effective amount of zinc oxide; and
    milling the mixture produce a dispersion concentrate of the immobilized 1,2-benzisothiazolin-3-one/zinc oxide complex.

24. An immobilized 1,2-benzisothiazolin-3-one/zinc oxide complex prepared by a method comprising:
    providing an aqueous mixture having a pH of about 7 to about 8.5 which includes water, 1,2-benzisothiazolin-3-one, zinc chloride and an immobilizing effective amount of zinc oxide; and
    milling the mixture to produce a dispersion concentrate which includes the immobilized 1,2-benzisothiazolin-3-one/zinc oxide complex.

\* \* \* \* \*